United States Patent
Lou et al.

(10) Patent No.: US 9,232,927 B2
(45) Date of Patent: Jan. 12, 2016

(54) METHOD OF RECONSTRUCTION FROM MULTI-ENERGY CT SCAN AND DEVICE THEREOF

(71) Applicant: Shenyang Neusoft Medical Systems Co., Ltd., Shenyang (CN)

(72) Inventors: Shanshan Lou, Shenyang (CN); Jiangwei Zhao, Shenyang (CN); Lixia Tong, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 236 days.

(21) Appl. No.: 13/974,074

(22) Filed: Aug. 23, 2013

(65) Prior Publication Data

US 2014/0064441 A1 Mar. 6, 2014

(30) Foreign Application Priority Data

Sep. 4, 2012 (CN) .......................... 2012 1 0324231

(51) Int. Cl.
*A61B 6/03* (2006.01)
*A61B 6/00* (2006.01)
*G06T 11/00* (2006.01)

(52) U.S. Cl.
CPC ............. *A61B 6/5205* (2013.01); *G06T 11/006* (2013.01); *A61B 6/032* (2013.01); *A61B 6/583* (2013.01); *G06T 2211/408* (2013.01)

(58) Field of Classification Search
CPC ........ A61B 6/032; A61B 6/405; A61B 6/482; A61B 6/583; A61B 6/5205; G06T 11/003; G01N 23/046
See application file for complete search history.

(56) References Cited

U.S. PATENT DOCUMENTS

| 2009/0208084 A1* | 8/2009 | Liu et al. ................. 382/131 |
| 2010/0008558 A1* | 1/2010 | Baeumer et al. ............. 382/131 |
| 2011/0129057 A1* | 6/2011 | Paul et al. ................ 378/4 |
| 2013/0182821 A1 | 7/2013 | Tsuyuki et al. |

FOREIGN PATENT DOCUMENTS

CN 103202707 A 7/2013

OTHER PUBLICATIONS

The first Office Action issued on Mar. 17, 2015 regarding the Chinese priority patent application (Appl. No. 201210324231.9) and a English summary, 7 pages.

\* cited by examiner

*Primary Examiner* — David J Makiya
*Assistant Examiner* — Julio M Duarte-Carvajalino
(74) *Attorney, Agent, or Firm* — Kilpatrick Townsend & Stockton LLP

(57) ABSTRACT

A method for collecting multi-energy CT data is provided. A method of reconstruction from multi-energy CT scan is further provided, in which data collection is performed on the first-class object at voltage values of m sampling points of the first-class voltage varied periodically, to obtain n sets of multi-energy first-class scan data $\{y_i\}$; and a data collection is performed on a double-cylinder correction phantom at the voltage values of m sampling points to obtain combination coefficients, and thus obtaining corresponding combination coefficients $C^i_{first}$ and $C^i_{second}$ corresponding to the case that the first-class scan data is collected in the $i^{th}$ projection angle at the first-class voltage; and the image vectors $X_{first}$ and $X_{second}$ are obtained by calculating a minimum value of the difference between the first-class scan data $\{y_i\}$ and the combination projection data $C^i_{first}P_i*X_{first}+C^i_{second}P_i*X_{second}$.

8 Claims, 4 Drawing Sheets

US 9,232,927 B2

METHOD OF RECONSTRUCTION FROM MULTI-ENERGY CT SCAN AND DEVICE THEREOF

This application claims the priority of Chinese Patent Application No. 201210324231.9, entitled "METHOD OF RECONSTRUCTION FROM MULTI-ENERGY CT SCAN AND DEVICE THEREOF", filed with the Chinese State Intellectual Property Office on Sep. 4, 2012, which is incorporated by reference in its entirety herein.

FIELD OF THE INVENTION

The invention relates to the field of Computed Tomography (CT), and particularly to a method of reconstruction from a multi-energy CT scan and a device thereof.

BACKGROUND OF THE INVENTION

Presently, CT scan is widely used in the field of medicine. Different tissue structures in a CT image can be discriminated by the different attenuations of x-rays with different energies in a material.

At present, generally there are two methods for collecting dual energy data. In one method, dual energy is achieved by rapidly switching tube voltages from projection to projection, thereby obtaining data for distinctive energies in an alternate way in respective projection directions during one scan. In the other method, a dual-source technology is applied, in which each of the tubes emits rays with a distinctive energy to obtain data for two different energies during one scan.

For one material, such as water or bone, x-ray beams with two different energies have different attenuations, and thus the pixel values of the obtained CT images are also different, by which two components can be discriminated in the image. For example, a CT image reconstruction may be performed from data obtained in a scan conducted at two different energies, resulting in two images I1 and I2. The proportions of water and bone at each point of the image may be simply calculated from the following two equations:

Water=Coeff1*I1+Coeff2*I2

Bone=Coeff3*I1+Coeff4*I2

If the combination coefficients Coeff1, Coeff2, Coeff3, Coeff4 are known, the proportions of water and bone can be easily calculated according to the images I1 and I2 respectively corresponding to two different beam energies. Generally, those coefficients are obtained by scanning a simple object for correction in advance and applying certain correction algorithms.

However, the process of obtaining the dual-energy data has a high hardware requirement. For example, in one of the two methods for collecting data described above, it is required to switch the tube voltages among different projections quickly, and in the other method it is required to provide two tubes.

SUMMARY OF THE INVENTION

In view of this, a major object of the invention is to provide a method for collecting multi-energy CT data, to solve the problem of the high hardware requirement involved in the method for collecting dual-energy data.

A method for collecting multi-energy CT data is provided according to the invention. The method includes:

scanning an object at a voltage periodically varied during data collection under the control of a CT scanner, wherein the voltage is varied for an entire period during the data collection.

Preferably, the scanning an object at a voltage periodically varied during data collection under the control of a CT scanner includes: scanning the object periodically at m different sampling points between a highest tube voltage and a lowest tube voltage, wherein m≥3.

Preferably, the scan is performed at the voltage which is varied periodically according to a first function $f(x)$ during the data collection, wherein the period of the first function $f(x)$ is 2 T, and the highest tube voltage and the lowest tube voltage may be reached in each period of the $f(x)$.

Preferably, the first function $f(x)$ may be:

$$f(x) = \begin{cases} \lfloor (MaxKV - MinKV) * |\sin(x\gamma)| + MinKV \rfloor & 0 \le x \le T \\ f(2*T - x) & T+1 \le x \le 2T-1 \end{cases}$$

wherein x is an integer, 2 T is a variation period of the voltage, $$\Omega = \frac{n}{4T}, \gamma = \frac{2\pi\Omega}{n},$$

MaxKV is the highest tube voltage, and MinKV is the lowest tube voltage.

A method of reconstruction from a multi-energy CT scan and a device thereof are provided according to the invention, whereby to achieve the purpose of obtaining multi-energy scan data in data collection conducted in a way that the voltage is varied periodically and reconstructing a tissue-discriminated image by using the multi-energy scan data. In this way, the high hardware requirement for reconstructing a tissue-discriminated image from dual-energy data is avoided.

A method of reconstruction from a multi-energy CT scan is provided according to the invention. The method includes a first data collecting step, a second data collecting step, a multi-energy correction step and a multi-energy image reconstruction step:

The first data collecting step includes:

setting a first-class object including a first material and a second material as the object to be scanned; performing data collection at a first-class voltage with the above method for collecting multi-energy CT data, to collect n sets of first-class scan data $\{y_i\}$ in n projection angles, wherein i is an integer, 1≤i≤n, n≥2, the first-class voltage is varied periodically during the data collection, m different sampling points are distributed between a highest tube voltage and a lowest tube voltage of the first-class voltage, performing a data collection at a first-class voltage includes performing the data collection periodically at the voltages of the m sampling points during the data collection.

The second data collecting step includes:

scanning a double-cylinder correction phantom in n projection angles respectively, at the respective voltages of the m sampling points with the CT scanner, to obtain m groups of data, each group including n sets of second-class scan data, wherein the double-cylinder correction phantom includes two materials to be discriminated in the first-class object, one cylinder includes a first material, and the other cylinder includes a second material.

The multi-energy correction step includes:
reconstructing and correcting m second-class images from the m groups of data wherein each group including n sets of second-class scan data, corresponds to one of the second-class images;
obtaining third-class images of the first material and third-class images of the second material according to the position and size of the first material and the second material in the double-cylinder correction phantom; and
calculating respective combination coefficients $M_{first}^H$ and $M_{second}^H$ corresponding to the voltage values of the m sampling points, according to m equations:

$M_{first}^H$ third-class image of first material+$M_{second}^H$ third-class image vector of second material =the $H^{th}$ second-class image, where H is $H^{th}$ sampling point of the m tube voltage, $H=0, 1, \ldots, m-1$.

The multi-energy image reconstruction step includes:
determining the image vectors $X_{first}$ and $X_{second}$ for which the difference between the first-class scan data $\{y_i\}$ and combination projection data $C_{first}^i P_{i*} X_{first} + C_{second}^i P_{i*} X_{second}$ reaches its minimum value.

Wherein $C_{first}^i$ and $C_{second}^i$ are combination coefficients corresponding to the case that the first-class scan data is collected at the first-class voltage in the $i^{th}$ projection angle, and $C_{first}^i$ and $C_{second}^i$ are obtained according to the respective combination coefficients $M_{first}^H$ and $M_{second}^H$ corresponding to the voltage values of the m sampling points, and
wherein $P_{i*}$ is the $i^{th}$ row of a projection matrix; and
determining the image vectors $X_{first}$ and $X_{second}$ for which the difference between the first-class scan data $\{y_i\}$ and the combination projection data $C_{first}^i P_{i*} X_{first} + C_{second}^i P_{i*} X_{second}$ has the minimum value, as the transpose of the first-class image vector of the first material and the transpose of the first-class image vector of the second material respectively.

A device of a reconstruction from a multi-energy CT scan is also provided according to the invention. The device includes:
a first data collecting unit adapted to set a first-class object containing a first material and a second material (maybe containing other materials) as object to be scanned; perform, using the method above for collecting multi-energy CT data, a data collection at a first-class voltage to collect n sets of first-class scan data $\{y_i\}$ in n projection angles, wherein i is an integer, $1 \leq i \leq n$, $n \geq 2$, the first-class voltage is varied periodically during the data collection, m different sampling points are distributed between a highest tube voltage and a lowest tube voltage of the first-class voltage, performing a data collection at a first-class voltage includes: performing the data collection periodically at the voltages of the m sampling points during the data collection; and send the n sets of the first-class scan data $\{y_i\}$ to a multi-energy image reconstruction unit;
a second data collecting unit adapted to scan a double-cylinder correction phantom in n projection angles respectively, at the respective voltages of the m sampling points with the CT scanner, to obtain m groups of data, each group including n sets of second-class scan data, wherein the double-cylinder correction phantom includes two materials to be discriminated in the first-class object, one cylinder includes a first material, and the other cylinder includes a second material; and send the m groups each including n sets of second-class scan data to a multi-energy correction unit;
the multi-energy correction unit adapted to reconstruct and correct m second-class images from the m groups of n sets of second-class scan data, wherein each group, including n sets of the second-class scan data corresponds to one of reconstructed and corrected second-class images; obtain a third-class image vector of the first material and a third-class image vector of the second material according to the position and size of the first material and the second material in the double-cylinder correction phantom; calculate respective combination coefficients $M_{first}^H$ and $M_{second}^H$ corresponding to the tube voltage values of the m sampling points, according to m equations: $M_{first}^H$ third-class image vector of first material+$M_{second}^H$ third-class image vector of second material=the $H^{th}$ second-class scan image; and send the respective combination coefficients $M_{first}^H$ and $M_{second}^H$ corresponding to the voltage values of the m sampling points to the multi-energy reconstruction unit, where H is $H^{th}$ sampling point of the m tube voltage, $H=0, 1, \ldots, m-1$; and
the multi-energy image reconstruction unit adapted to obtain image vectors $X_{first}$ and $X_{second}$ for which a difference between the first-class scan data $\{y_i\}$ and combination projection data $C_{first}^i P_{i*} X_{first} + C_{second}^i P_{i*} X_{second}$ has a minimum value, wherein $C_{first}^i$ and $C_{second}^i$ are combination coefficients corresponding to the case that the first-class scan data is collected in the $i^{th}$ projection angle at the first-class voltage, and $C_{first}^i$ and $C_{second}^i$ are obtained according to the respective combination coefficients $M_{first}^H$ and $M_{second}^H$ corresponding to the voltage values of the m sampling points, and $P_{i*}$ is the $i^{th}$ row of a projection matrix; determine the image vectors $X_{first}$ and $X_{second}$ for which a difference between the first-class scan data $\{y_i\}$ and the combination projection data $C_{first}^i P_{i*} X_{first} + C_{second}^i P_{i*} X_{second}$ is the minimum value, as the transpose of the first-class image vector of the first material and the transpose of the first-class image vector of the second material respectively.

The invention has advantageous effects as follows.

According to the method for collecting multi-energy CT data provided by the invention, the object is scanned at a tube voltage periodically varied during the data collection, thereby avoiding the problem of high hardware requirement in the method for collecting dual-energy data. In addition, a method of reconstruction from multi-energy CT scan and a device thereof are also provided according to the invention. In the method of reconstruction from multi-energy CT scan, a data collection is performed on the first-class object including the first material and the second material (maybe containing other materials) at voltage values of m sampling points of a first-class voltage which is varied periodically, and thus n sets of multi-energy first-class scan data $\{y_i\}$ is obtained. A data collection is performed on a double-cylinder correction phantom including the two materials to be discriminated in the first-class object, at the voltage values of the m sampling points, to obtain respective combination coefficients $M_{first}^H$ and $M_{second}^H$ corresponding to the voltage values of the m sampling points and obtain corresponding combination coefficients $C_{first}^i$ and $C_{second}^i$ in the case that the first-class scan data is collected at the first-class voltage in the $i^{th}$ projection angle. The image vectors $X_{first}$ and $X_{second}$ for which the difference between the first-class scan data $\{y_i\}$ and combination projection data $C_{first}^i P_{i*} X_{first} + C_{second}^i P_{i*} X_{second}$ has the minimum value are obtained by calculating the minimum value of the difference between the first-class scan data $\{y_i\}$ and combination projection data $C_{first}^i P_{i*} X_{first} + C_{second}^i P_{i*} X_{second}$. The image vectors $X_{first}$ and $X_{second}$ for which a difference between the first-class scan data $\{y_i\}$ and the combination projection data $C_{first}^i P_{i*} X_{first} + C_{second}^i P_{i*} X_{second}$ has the minimum value are determined as the transpose of the first-class image vectors of the first material and the transpose of the first-class image vectors of the second material respectively. It can be seen that, with the method of reconstruction from multi-energy CT scan and the device thereof according to the invention, the multi-energy scan data can be obtained in the way that the voltage is varied periodically (maybe slowly). The tissue-discriminated image, including the first-class image vector of the first material and the first-class image vector of the second material, is reconstructed from the multi-energy scan data. Energies for performing the projections may be switched quickly between a high voltage and a low voltage, or may be varied gradually, so that multiple projections may be performed during the variation of the voltage from the high voltage to the low voltage. In this way, the high hardware requirement for obtaining the dual-energy data is avoided.

DETAILED DESCRIPTION OF THE INVENTION

In order to better understand the above purpose, features and advantages of the present invention, embodiments of the present invention will be explained in detail in conjunction with drawings and specific implementations.

A method for collecting multi-energy CT data is provided according to the invention. The method includes:

scanning an object at a tube voltage periodically varied during data collection under the control of a CT scanner, in which the voltage during the data collection is varied for an entire period.

In a preferred embodiment of the invention, scanning an object at a tube voltage periodically varied during data collection under the control of a CT scanner includes scanning the object periodically at m different sampling points between a highest tube voltage and a lowest tube voltage, where $m \geq 3$.

In another preferred embodiment of the invention, it is proposed that the scanning is preformed at the voltage controlled to be varied periodically according to a first function $f(x)$ during the data collection, where a period of the first function $f(x)$ is 2 T, and $f(x)$ have a highest tube voltage and a lowest tube voltage in each period. Specifically, in one preferred embodiment, the first function $f(x)$ may be:

$$f(x) = \begin{cases} \lfloor (MaxKV - MinKV) * |\sin(x\gamma)| + MinKV \rfloor & 0 \leq x \leq T \\ f(2*T - x) & T + 1 \leq x \leq 2T - 1 \end{cases}$$

where x is an integer, 2 T is a variation period of the voltage, $$\Omega = \frac{n}{4T}, \gamma = \frac{2\pi\Omega}{n},$$

MaxKV is the highest tube voltage, and MinKV is the lowest tube voltage.

Figure 1:
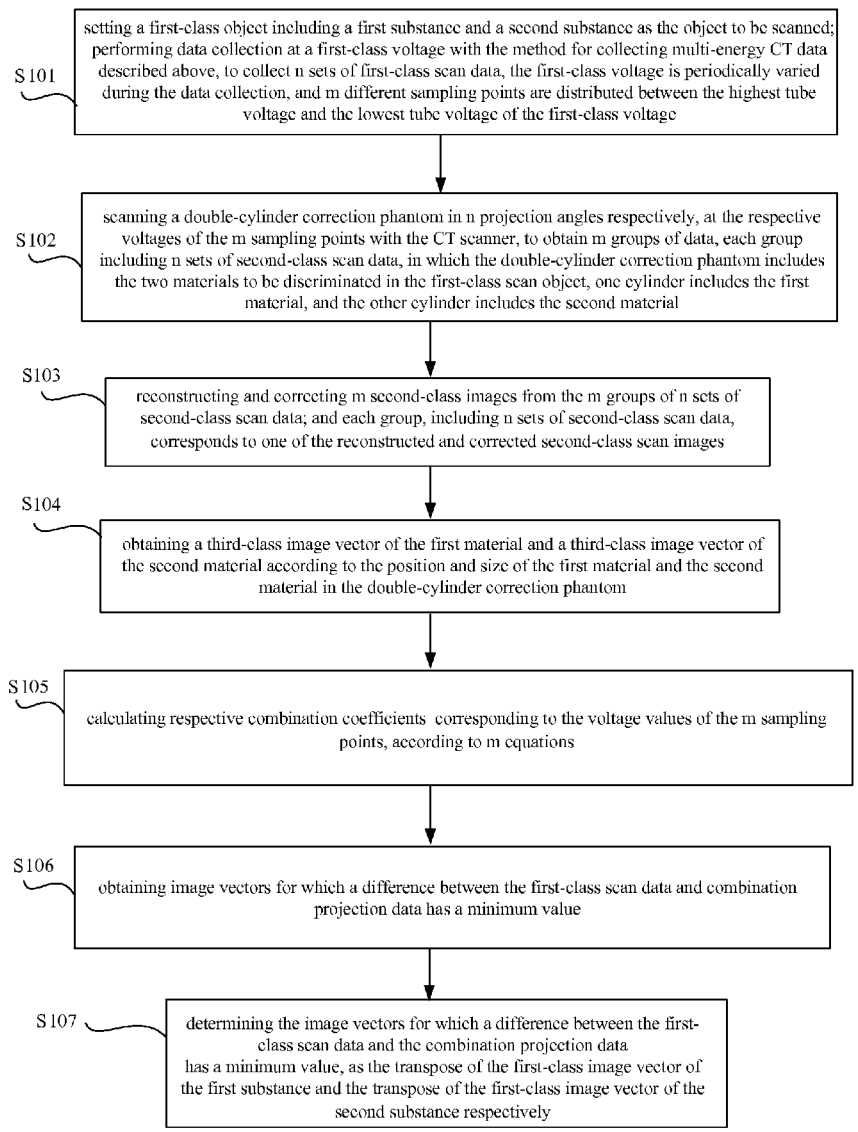
FIG. 1 is a diagram showing steps of a method of reconstruction from multi-energy CT scan according to the invention.

A method of reconstruction from a multi-energy CT scan is provided according to the invention. Referring to FIG. 1, the method includes a first data collecting step, a second collecting step, a multi-energy correction step and a multi-energy image reconstruction step.

The first data collecting step includes step S101.

S101, setting a first-class object including a first material and a second material (maybe containing other materials) as the object to be scanned; performing data collection at a first-class voltage with the method for collecting multi-energy CT data described above, to collect n sets of first-class scan data $\{y_i\}$ in n projection angles, where i is an integer, $1 \leq i \leq n$, $n \geq 2$, the first-class voltage is varied periodically during the data collection, and m different sampling points are distributed between the highest tube voltage and the lowest tube voltage of the first-class voltage. Performing the data collection at the first-class voltage includes performing the data collection periodically at the voltages of the m sampling points during the data collection.

This step is directed to a process for performing the data collection on the first-class object. It is assumed that for a round of collection n projections are performed, and the collected n sets of first-class scan data $\{y_i\}$ are multi-energy data, where i indicates the $i^{th}$ projection angle, and $y_i$ indicates the first-class scan data in the $i^{th}$ projection angle, which is obtained by performing the data collection on the first-class object with the CT scanner in the method for collecting multi-energy CT data described above in a way that the voltage is varied periodically.

The second data collecting step includes step S102.

S102, scanning a double-cylinder correction phantom in n projection angles respectively, at the respective voltages of the m sampling points with the CT scanner, to obtain m groups of data, each group including n sets of second-class scan data, in which the double-cylinder correction phantom includes the two materials to be discriminated in the first-class object, one cylinder includes the first material, and the other cylinder includes the second material.

In this step, in scanning the double-cylinder correction phantom in n projection angles respectively at the respective voltages of the m sampling points with the CT scanner, a round of data collection is performed on the double-cylinder correction phantom at the voltage value of each of the m sampling points. Namely, the scan is performed at the voltage value of each of m sampling points in n projection angles, and thus m groups of data are obtained, each group including n sets of the second-class scan data.

Figure 2:
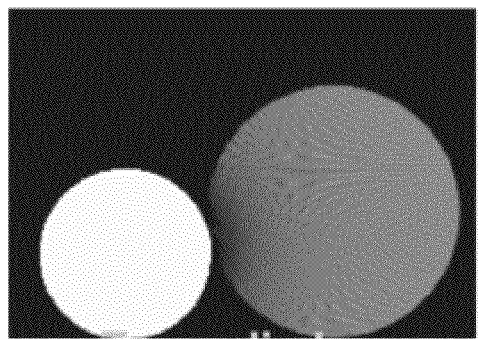
FIG. 2 is a schematic diagram of a double-cylinder correction phantom according to the invention.

The double-cylinder correction phantom may be a double-cylinder correction phantom shown in FIG. 2, in which the materials of two cylinders are the materials to be discriminated, respectively, for example water and bone.

The multi-energy correction step includes the steps S103, S104 and S105.

S103, reconstructing and correcting m second-class images from the m groups of n sets of second-class scan data. Each group, including n sets of second-class scan data, corresponds to one of the reconstructed and corrected second-class scan images.

In this step, reconstructing and correcting one corresponding second-class image from one group including n sets of second-class scan data can be performed by using the reconstruction and beam hardening correction methods known in the prior art, such as a convolution back projection Algorithm and a water precorrection.

S104, obtaining a third-class image vector of the first material and a third-class image vector of the second material according to the position and size of the first material and the second material in the double-cylinder correction phantom.

In this step, which pixels in the images correspond to the first material and which pixels in the images correspond to the second material may be determined from the geometric positions and the geometric dimensions of the first material and the second material. A threshold-division is simply performed on any one of the second-class scan images obtained in the step S103, to obtain the third-class image vector of the first material and the third-class image vector of the second material. In the third-class image of the first material, the pixel values corresponding to the first material are 1, and the pixel values corresponding to the other material except the first material are 0. In the third image of the second material, the pixel values corresponding to the second material are 1, and the pixel values corresponding to the other material except the second material are 0.

S105, calculating respective combination coefficients $M_{first}^{H}$ and $M_{second}^{H}$ corresponding to the voltage values of the m sampling points, according to m equations:

$M_{first}^{H}$ third-class image vector of first material+
$M_{second}^{H}$ third-class image vector of second material=the $H^{th}$ second-class scan image, where H is $H^{th}$ sampling point of the m tube voltage, H=0, 1, ..., m−1.

In this step, the combination coefficients $M_{first}^{H}$ and $M_{second}^{H}$ may be calculated using the least square method. Specifically, $M_{first}^{H}$ is a combination coefficient corresponding to the first material when the data collection is performed at the voltage value of the $H^{th}$ sampling point in m sampling points, and $M_{second}^{H}$ is a combination coefficient corresponding to the second material when the data collection is performed at the voltage value of the $H^{th}$ sampling point in m sampling points.

The multi-energy reconstruction step includes the steps S106 and S107.

S106, obtaining image vectors $X_{first}$ and $X_{second}$ for which a difference between the first-class scan data $\{y_i\}$ and combination projection data $C_{first}^{i} P_{i*} X_{first} + C_{second}^{i} P_{i*} X_{second}$ has a minimum value.

The $C_{first}^{i}$ and $C_{second}^{i}$ are combination coefficients corresponding to the case that the first-class scan data $\{y_i\}$ is collected at the first-class voltage in the $i^{th}$ projection angle, and $C_{first}^{i}$ and $C_{second}^{i}$ are obtained according to respective combination coefficients $M_{first}^{H}$ and $M_{second}^{H}$ corresponding to the voltage values of the m sampling points.

$P_{i*}$ is the $i^{th}$ row of a projection matrix.

It should be noted as following.

(1) $C_{first}^{i}$ and $C_{second}^{i}$ are combination coefficients corresponding to the case that the first-class scan data is collected in the $i^{th}$ projection angle at the first-class voltage, $C_{first}^{i}$ is a combination coefficient corresponding to the first material, and $C_{second}^{i}$ is a combination coefficient corresponding to the second material, and performing the data collection at the first-class voltage specifically includes performing the data collection periodically at the voltage values of the m sampling points during the data collection. Thus, $C_{first}^{i}$ and $C_{second}^{i}$ may be obtained according to the respective combination coefficients $M_{first}^{H}$ and $M_{second}^{H}$ corresponding to the voltage values of the m sampling points.

For example, the combination coefficient $M_{first}^{H}$ corresponding to the voltage value of each of m sampling points is one of $M_{first}^{0}$ to $M_{first}^{m}$, and the combination coefficient $M_{second}^{H}$ is one of $M_{second}^{0}$ to $M_{second}^{m}$.

In this way, in the data collection, when the first-class scan data is collected at the first-class voltage in the projection angles within the first variation period, the corresponding combination coefficients include:
the combination coefficient corresponding to the first material: $M_{first}^{0}$ to $M_{first}^{m}$, $M_{first}^{m-1}$ to $M_{first}^{1}$; and
the combination coefficient corresponding to the second material: $M_{second}^{0}$ to $M_{second}^{m}$, $M_{second}^{m-1}$ to $M_{second}^{1}$.

Repeating this process sequentially, the combination coefficients corresponding to the case that the first-class scan data is collected at the first-class voltage in the projection angles within the subsequent variation periods may be obtained, and then $C_{first}^{i}$ and $C_{second}^{i}$ are obtained.

(2) The projection matrix P may be calculated with an existing method in the art. For example, the length of a line segment that one ray overlaps a pixel may be a element of the projection matrix P. the length of the overlapped line can be calculated according to a geometric relationship among the coordinate of each pixel in medical image of the first-class object, the coordinate of the x-ray source for emitting the x-rays, and the coordinate of each detector in the CT scanner, so as to obtain the projection matrix P.

S107, determining the image vectors $X_{first}$ and $X_{second}$ for which a difference between the first-class scan data $\{y_i\}$ and the combination projection data $C_{first}^{i} P_{i*} X_{first} + C_{second}^{i} P_{i*} X_{second}$ has a minimum value, as the transpose of the first-class image vector of the first material and the transpose of the first-class image vector of the second material, respectively.

It can be seen from the specific embodiment described above that, in the method of reconstruction from multi-energy CT scan provided by the invention, the energies for the projections may be switched quickly between a high voltage and a low voltage, or may be varied gradually, so that multiple projections may be conducted in the process that the voltage is varied from the high voltage to the low voltage, thus avoiding the high hardware requirement for obtaining the dual-energy data.

Preferably, in a preferred embodiment of the invention, the energies for the projections may be varied gradually. In this embodiment, the number m of different sampling points between the highest voltage and the lowest voltage of the first-class voltage is equal to or greater than 3.

In the following, the calculation of the minimum value of the difference between the first-class scan data $\{y_i\}$ and combination projection data $C_{first}^{i} P_{i*} X_{first} + C_{second}^{i} P_{i*} X_{second}$ in the multi-energy image reconstruction step will be described in detail. It should be noted that, the multi-energy image reconstruction step to be described below is not only applicable to the case that the energies for the projections are switched quickly between a high voltage and a low voltage, but also applicable to the case that the energies for obtaining the projections are varied gradually.

In this preferred embodiment of the invention, in calculating the minimum value of the difference between the first-class scan data $\{y_i\}$ and the combination projection data $C_{first}^{i} P_{i*} X_{first} + C_{second}^{i} P_{i*} X_{second}$, a minimum value of an objective function $$\psi(X_{first}, X_{second}) = \frac{1}{2} \sum_{i} \left( y_i - \begin{pmatrix} C_{first}^{i} P_{i*} X_{first} + \\ C_{second}^{i} P_{i*} X_{second} \end{pmatrix} \right)^2 + \beta(\|X_{first}\|_{TV} + \|X_{second}\|_{TV})$$

is calculated, where $$\frac{1}{2} \sum_{i} \left( y_i - \begin{pmatrix} C_{first}^{i} P_{i*} X_{first} + \\ C_{second}^{i} P_{i*} X_{second} \end{pmatrix} \right)^2$$

is a difference term which is used to determine the difference between $\{y_i\}$ and $C_{first}^i P_{i*} X_{first}^n + C_{second}^i P_{i*} X_{second}$, and $\beta(\|X_{first}\|_{TV} + \|X_{second}\|_{TV})$ is a regularization term, in which $\beta$ is a compromise parameter. The obtained objective image vectors $X_{first}$ and $X_{second}$ may have a certain degree of smoothness by determining a proper value of the compromise parameter $\beta$. The larger value of $\beta$ results in smoother image and lower resolution. In contrast, the smaller value of $\beta$ results in greater noise of the finally image and higher resolution. In the specific implementation of the invention, $\beta$ should be appropriately adjusted as needed, so that the image can satisfy the requirement in resolution. $\|\cdot\|_{TV}$ indicates a total variation.

Figure 3:
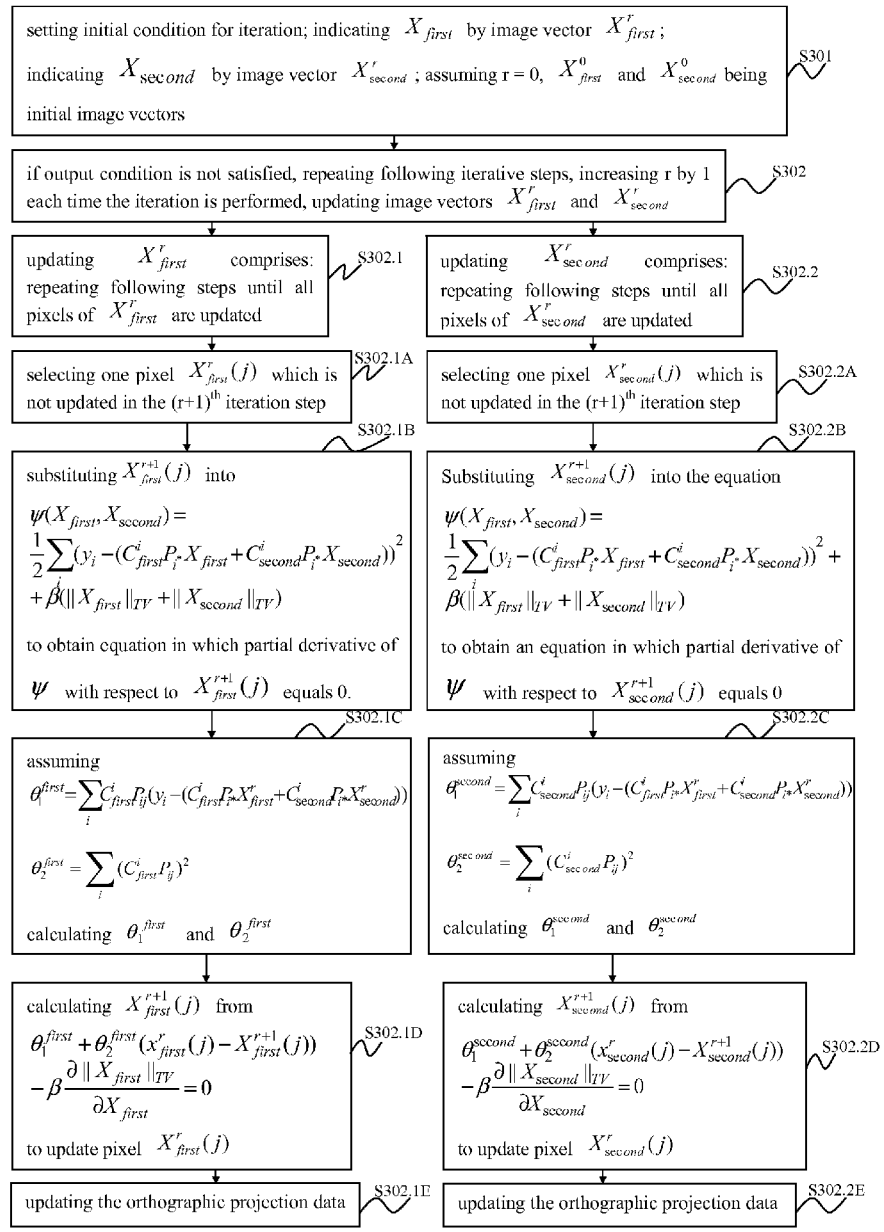
FIG. 3 is a diagram showing steps for performing a cyclic iteration of $X_{first}$ and $X_{second}$ according to the invention.

In a preferred embodiment of the invention, the minimum value of the objective function $$\psi(X_{first}, X_{second}) =$$
$$\frac{1}{2}\sum_i \left(y_i - \begin{pmatrix} C_{first}^i P_{i*} X_{first} + \\ C_{second}^i P_{i*} X_{second} \end{pmatrix}\right)^2 + \beta(\|X_{first}\|_{TV} + \|X_{second}\|_{TV})$$

is calculated by performing a cyclic iteration on the image vectors $X_{first}$ and $X_{second}$, as shown in FIG. 3. The cyclic iteration specifically includes steps S301 to S302.

S301, setting initial conditions for the iteration.

$X_{first}$ is indicated by an image vector $X_{first}^r$.

$X_{second}$ is indicated by an image vector $X_{second}^r$.

It is defined that r=0, $X_{first}^0$, and $X_{second}^0$ are initial image vectors which may specifically be the $0^{th}$ image.

An orthographic projection is performed on $X_{first}^0$ with the projection matrix P to obtain initial orthographic projection data $q_{first}^0 = P \cdot X_{first}^0$. An orthographic projection is performed on $X_{second}^0$ with the projection matrix P to obtain initial orthographic projection data $q_{second}^0 = P \cdot X_{second}^0$.

S302, performing the iterative steps from r=0.

If an output condition is not satisfied, the following iterative steps are repeated, where the current iteration is the $(r+1)^{th}$ iteration, $X_{first}^{r+1}$ indicates the image vector $X_{first}$ obtained in the $(r+1)^{th}$ iteration, and $X_{first}^r$ indicates the image vector $X_{first}$ before the $(r+1)^{th}$ iteration $(r^{th})$. $X_{second}^{r+1}$ indicates the image vector $X_{second}$ obtained in the $(r+1)^{th}$ iteration, and $X_{second}^r$ indicates the image vector $X_{second}$ before the $(r+1)^{th}$ iteration $(r^{th})$. The value of r is increased by 1 each time the iteration is performed. The iterative steps include updating the image vector $X_{first}^r$ and updating the image vector $X_{second}^r$.

S302.1, the step of updating the $X_{first}^r$ includes:

repeating the following steps S302.1A to S302.1E until all pixels of $X_{first}^r$ are updated.

S302.1A, selecting one pixel $X_{first}^r(j)$ which is not updated in the $(r+1)^{th}$ iteration step, from the image vector $X_{first}^r$.

S302.1B, substituting $X_{first}^{r+1}(j)$ into the equation $$\psi(X_{first}, X_{second}) =$$
$$\frac{1}{2}\sum_i \left(y_i - \begin{pmatrix} C_{first}^i P_{i*} X_{first} + \\ C_{second}^i P_{i*} X_{second} \end{pmatrix}\right)^2 + \beta(\|X_{first}\|_{TV} + \|X_{second}\|_{TV})$$

to obtain an equation in which a partial derivative of $\psi$ with respect to $X_{first}^{r+1}(j)$ is equal to 0:

$$\sum_i C_{first}^i P_{ij}\left(y_i - \begin{pmatrix} C_{first}^i P_{i*} X_{first}^r + \\ C_{second}^i P_{i*} X_{second}^r \end{pmatrix}\right) +$$

$$(X_{first}^r(j) - X_{first}^{r+1}(j))\sum_i (C_{first}^i P_{ij})^2 - \beta \frac{\partial \|X_{first}^r\|_{TV}}{\partial X_{first}^{r+1}(j)} = 0.$$

S302.1C, assuming:

$$\theta_1^{first} = \sum_i C_{first}^i P_{ij}(y_i - (C_{first}^i P_{i*} X_{first}^r + C_{second}^i P_{i*} X_{second}^r))$$

$$\theta_2^{first} = \sum_i (C_{first}^i P_{ij})^2,$$

where $P_{ij}$ is a projection coefficient in the $i^{th}$ row and the $j^{th}$ column of the projection matrix P;

calculating $\theta_1^{first}$ and $\theta_2^{first}$, under the conditions that $P_{i*} X_{first}^r$ equals the $i^{th}$ row of the projection data $q_{first}^r$ and $P_{i*} X_{second}^r$ equals the $i^{th}$ row of the projection data $q_{second}^r$.

S302.1D, calculating $X_{first}^{r+1}(j)$ from $$\theta_1^{first} + \theta_2^{first}(x_{first}^r(j) - X_{first}^{r+1}(j)) - \beta \frac{\partial \|X_{first}\|_{TV}}{\partial X_{first}} = 0$$

in a dichotomy method to update the pixel $X_{first}^r(j)$.

Herein, $X_{first}^{r+1}(j)$ is calculated, the update of the pixel $X_{first}^r(j)$ is completed, and the updated image vector $X_{first}^{r+1}$ is obtained.

S302.1E, updating the orthographic projection data by $$q_{first}^{r+1} = q_{first}^r + P \cdot (X_{first}^{r+1} - X_{first}^r).$$

S302.2, the step of updating the $X_{second}^r$ includes:

repeating the following steps S302.2A to S302.2E until all pixels of $X_{second}^r$ are updated.

S302.2A, selecting one pixel $X_{second}^r(j)$ which is not updated in the $(r+1)^{th}$ iteration step, from the image vector $X_{second}^r$.

S302.2B, substituting $X_{second}^{r+1}(j)$ into the equation $$\psi(X_{first}, X_{second}) =$$
$$\frac{1}{2}\sum_i \left(y_i - \begin{pmatrix} C_{first}^i P_{i*} X_{first} + \\ C_{second}^i P_{i*} X_{second} \end{pmatrix}\right)^2 + \beta(\|X_{first}\|_{TV} + \|X_{second}\|_{TV})$$

to obtain an equation in which a partial derivative of $\psi$ with respect to $X_{second}^{r+1}(j)$ equals 0:

$$\sum_i C_{second}^i P_{ij}(y_i - (C_{first}^i P_i * X_{first}^r + C_{second}^i P_i * X_{second}^r)) +$$

$$(X_{second}^r(j) - X_{second}^{r+1}(j))\sum_i (C_{second}^i P_{ij})^2 - \beta \frac{\partial \|X_{second}^r\|_{TV}}{\partial X_{second}^{r+1}(j)} = 0$$

S302.2C, assuming:

$$\theta_1^{second} = \sum_i C_{second}^i P_{ij}(y_i - (C_{first}^i P_i * X_{first}^r + C_{second}^i P_i * X_{second}^r))$$

$$\theta_2^{second} = \sum_i (C_{second}^i P_{ij})^2,$$

where $P_{ij}$ is a projection coefficient in the $i^{th}$ row and the $j^{th}$ column of the projection matrix P;

calculating $\theta_1^{second}$ and $\theta_2^{second}$ under the conditions that $P_{i*} X_{first}^r$ equals the $i^{th}$ row of the projection data $q_{first}^r$ and $P_{i*}X_{second}{}^r$ equals the $i^{th}$ row of the projection data $q_{second}{}^r$.

S302.2D, calculating $X_{second}{}^{r+1}(j)$ from $$\theta_1^{second} + \theta_2^{second}(x_{second}^r(j) - X_{second}^{r+1}(j)) - \beta\frac{\partial\|X_{second}\|_{TV}}{\partial X_{second}} = 0$$

in a dichotomy method to update the pixel $X_{second}{}^r(j)$.

Here, $X_{second}{}^{r+1}(j)$ is calculated, the update of the pixel $X_{second}{}^r(j)$ is completed and the updated image vector $X_{second}{}^{r+1}$ is obtained.

S302.2E, updating the orthographic projection data by $q_{second}{}^{r+1} = q_{second}{}^r + P \cdot (X_{second}{}^{r+1} - X_{second}{}^r)$.

It should be noted that, a condition for repeating the iterative steps is that the output condition is not satisfied. The output condition may specifically be set as $\|X_{first}{}^{r+1} - X_{first}{}^r\| < \epsilon$ and $\|X_{second}{}^{r+1} - X_{second}{}^r\| < \epsilon$, where $\epsilon$ is a preset small threshold. In theory, the smaller the $\epsilon$ is, the better the image quality is. In the invention, it is verified by experiments that the image qualities of $X_{first}{}^{r+1}$ and $X_{second}{}^{r+1}$ finally obtained by iterative optimization are better in the case where the preset small threshold is at least less than $10^{-3}$.

Figure 4:
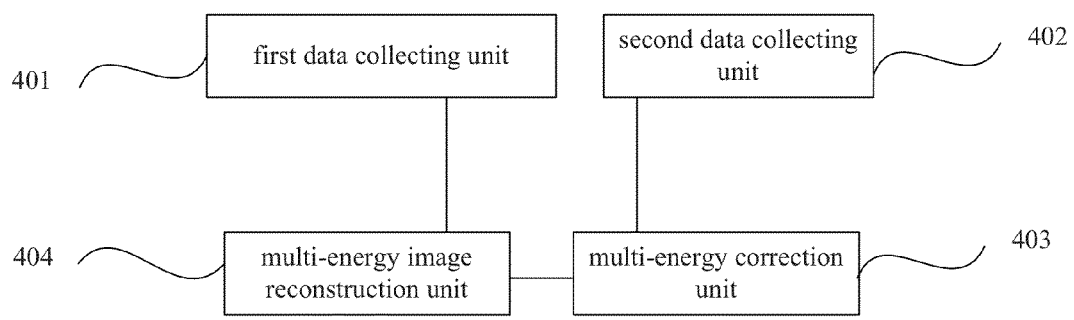
FIG. 4 is a diagram showing components of a device of reconstruction from a multi-energy CT scan according to the invention.

In the invention a device of reconstruction from multi-energy CT scan is further provided. Referring to FIG. 4, the device includes a first collecting unit 401, a second collecting unit 402, a multi-energy correction unit 403 and a multi-energy reconstruction unit 404.

The first collecting unit 401 is adapted to set a first-class object including a first material and a second material as the object to be scanned; perform data collection at a first-class voltage with the method for collecting multi-energy CT data described above, to collect n sets of first-class scan data $\{y_i\}$ at n projection angles, where i is an integer, $1 \le i \le n$, $n \ge 2$ the first-class voltage is varied periodically during the data collection, m different sampling points are distributed between a highest voltage and a lowest voltage of the first-class voltage, and performing the data collection at the first-class voltage includes performing the data collection periodically at the voltages of the m sampling points during the data collection; and send the n sets of the first-class scan data $\{y_i\}$ to the multi-energy image reconstruction unit 404.

The second collecting unit 402 is adapted to scan a double-cylinder correction phantom in n projection angles respectively, at the respective voltages of the m sampling points with the CT scanner, to obtain m groups of data, each group including n sets of second-class scan data, in which the double-cylinder correction phantom includes the two materials to be discriminated in the first-class object, one cylinder includes the first material, and the other cylinder includes the second material; and send the m groups of data to the multi-energy correction unit 403, each group including n sets of second-class scan data.

The multi-energy correction unit 403 is adapted to reconstruct and correct m second-class scan images from the m groups of n sets of second-class scan data, where each group, including n sets of second-class scan data, corresponds to one of the reconstructed and corrected second-class scan images; obtaining a third-class image vector of the first material and a third-class image vector of the second material according to the position and size of the first material and the second material in the double-cylinder correction phantom; calculate respective combination coefficients $M_{first}{}^H$ and $M_{second}{}^H$ corresponding to the voltage values of the m sampling points, according to m equations: $M_{first}{}^H$ third-class image vector of first material + $M_{second}{}^H$ third-class image vector of second material = the $H^{th}$ second-class scan image; and send the respective combination coefficients $M_{first}{}^H$ and $M_{second}{}^H$ corresponding to the voltage values of the m sampling points to the multi-energy reconstruction unit 404.

The multi-energy reconstruction unit 404 is adapted to obtain image vectors $X_{first}$ and $X_{second}$ for which a difference between the first-class scan data $\{y_i\}$ and combination projection data $C_{first}{}^i P_{i*} X_{first} + C_{second}{}^i P_{i*} X_{second}$ has a minimum value, by calculating the minimum value of the difference between the first-class scan data $\{y_i\}$ and the combination projection data $C_{first}{}^i P_{i*} X_{first} + C_{second}{}^i P_{i*} X_{second}$, where $C_{first}{}^i$ and $C_{second}{}^i$ are combination coefficients corresponding to the case that the first-class scan data is collected at the first-class voltage in the $i^{th}$ projection angle, and $C_{first}{}^i$ and $C_{second}{}^i$ are obtained according to the respective combination coefficients $M_{first}{}^H$ and $M_{second}{}^H$ corresponding to the voltage values of the m sampling points, and $P_{i*}$ is the $i^{th}$ row of a projection matrix; determine the image vectors $X_{first}$ and $X_{second}$ for which a difference between the first-class scan data $\{y_i\}$ and combination projection data $C_{first}{}^i P_{i*} X_{first} + C_{second}{}^i P_{i*} X_{second}$ has a minimum value, as the transpose of the first-class image vector of the first material and the transpose of the first-class image vector of the second material respectively.

It should be noted in the present disclosure that relational terms, such as "the first" and "the second", are only used to distinguish one entity or operation from another entity or operation, but not request or imply that there is any of such kind of practical relationship or order between these entities or operations. Moreover, terms such as "include", "contain" or any other variations thereof, are intended to cover a non-exclusive containing, such that a process, method, article or device including a series of elements, includes not only those elements, but also other elements which are not listed explicitly, or also includes elements which is inherent to the process, method, article or device. In the cases where there are no further limits, elements limited by a sentence "includes one . . . " does not exclude the presence of other same elements in the process, method, article or device including the elements.

The aforementioned disclosures are only preferred embodiments of the present disclosure, which are not intended to limit the scope of protection of the present disclosure. Any modification, replacement, improvement and the like made within the spirit and principle of the present disclosure fall within the scope of protection of the present disclosure.

The invention claimed is:

1. A method of reconstruction from a multi-energy CT scan, comprising a first data collecting step, a second data collecting step, a multi-energy correction step and a multi-energy image reconstruction step, wherein the first data collecting step comprises:

setting a first-class object comprising a first material and a second material as an object to be scanned; performing data collection at a first-class voltage with a method for collecting multi-energy CT data, to collect n sets of first-class scan data $\{y_i\}$ in n projection angles, wherein $i$ is an integer, $1 \le i \le n$, $n \ge 2$ the first-class voltage is varied periodically during the data collection, m different sampling points are distributed between a highest tube voltage and a lowest tube voltage of the first-class voltage, performing a data collection at a first-class voltage comprises performing the data collection periodically at the voltages of the m sampling points during the data collection;

the second data collecting step comprises:
scanning a double-cylinder correction phantom in n projection angles respectively, at the respective voltages of the m sampling points with the CT scanner, to obtain m groups of data, each group comprising n sets of second-class scan data, wherein the double-cylinder correction phantom comprises two materials to be discriminated in the first-class object, one cylinder comprises a first material, and the other cylinder comprises a second material;
the multi-energy correction step comprises:
reconstructing and correcting m second-class images from the m groups of data each group comprising n sets of second-class scan data, wherein each group including n sets of second-class scan data, corresponds to one of the second-class images;
obtaining third-class images of the first material and third-class images of the second material according to the position and size of the first material and the second material in the double-cylinder correction phantom; and
calculating respective combination coefficients $M^H_{first}$ and $M^H_{second}$ corresponding to the voltage values of the m sampling points, according to m equations: $M^H_{first}$ third-class image of first material $+M^H_{second}$ third-class image of second material $=$ the $H^{th}$ second-class scan image, wherein H is $H^{th}$ sampling point of the m tube voltage, H=0,1, . . . , m−1;
the multi-energy image reconstruction step comprises:
determining the image vectors $X_{first}$ and $X_{second}$ for which a difference between the first-class scan data $\{y_i\}$ and combination projection data $C^i_{first}P_{i*}X_{first} + C^i_{second}P_{i*}X_{second}$ reaches its minimum value,
wherein $C^i_{first}$ and $C^i_{second}$ are combination coefficients corresponding to the case that the first-class scan data is collected at the first-class voltage in the $i^{th}$ projection angle, and $C^i_{first}$ and $C^i_{second}$ are obtained according to the respective combination coefficients $M^H_{first}$ and $M^H_{second}$ corresponding to the voltage values of the m sampling points; and
$P_{i*}$ is the $i^{th}$ row of a projection matrix; and
determining the image vectors $X_{first}$ and $X_{second}$ for which the difference between the first-class scan data $\{y_i\}$ and the combination projection data $C^i_{first}P_{i*}X_{first} + C^i_{second}P_{i*}X_{second}$ has the minimum value, as the transpose of the first-class image vector of the first material and the transpose of the first-class image vector of the second material respectively;
displaying the reconstructed image on a display unit.

2. The method according to claim 1, wherein the number m of different sampling points of the first-class voltage between the highest tube voltage and the lowest tube voltage is equal to or greater than 3.

3. The method according to claim 1, wherein the determining the image vectors $X_{first}$ and $X_{second}$ for which a difference between the first-class scan data $\{y_i\}$ and combination projection data $C^i_{first}P_{i*}X_{first} + C^i_{second}P_{i*}X_{second}$ reaches its minimum value comprises:
calculating a minimum value of an objective function $$\psi(X_{first}, X_{second}) = \frac{1}{2}\sum_i (y_i - (C^i_{first}P_i * X_{first} + C^i_{second}P_i * X_{second}))^2 + \beta(\|X_{first}\|_{TV} + \|X_{second}\|_{TV}),$$

wherein β is a compromise parameter.

4. The method according to claim 3, wherein calculating the minimum value of the objective function $$\psi(X_{first}, X_{second}) = \frac{1}{2}\sum_i (y_i - (C^i_{first}P_i * X_{first} + C^i_{second}P_i * X_{second}))^2 + \beta(\|X_{first}\|_{TV} + \|X_{second}\|_{TV})$$

comprises:
indicating $X_{first}$ by an image vector $X_{first}^r$;
indicating $X_{second}$ by an image vector $X_{second}^r$;
assuming r =0, $X_{first}^0$ and $X_{second}^0$ being initial image vectors;
performing an orthographic projection on $X_{first}^0$ by the projection matrix P to obtain initial orthographic projection data $q_{first}^0 = P \cdot X_{first}^0$; performing an orthographic projection on $X_{second}^0$ by the projection matrix P to obtain initial orthographic projection data $q_{second}^0 = P \cdot X_{second}^0$;
if an output condition is not satisfied, repeating iterative steps, wherein the current iteration is the $(r+1)^{th}$ iteration, $X_{first}^{r+1}$ indicates the image vector $X_{first}$ obtained in the $(r+1)^{th}$ iteration, and $X_{first}^r$ indicates the image vector $X_{first}$ before the $(r+1)^{th}$ iteration, $X_{second}^{r+1}$ indicates the image vector $X_{second}$ obtained in the $(r+1)^{th}$ iteration, and $X_{second}^r$ indicates the image vector $X_{second}$ before the $(r+1)^{th}$ iteration; the value of r is increased by 1 each time the iterative steps are performed, the iterative steps comprise: updating the image vector $X_{first}^r$ and updating the image vector $X_{second}^r$, wherein
the step of updating the $X_{first}^r$ comprises:
repeating the following steps until all pixels of $X_{first}^r$ are updated;
selecting one pixel $X_{first}^r(j)$ which is not updated in the $(r+1)^{th}$ iteration step, from the image vector $X_{first}^r$;
substituting $X_{first}^{r+1}(j)$ into the equation $$\psi(X_{first}, X_{second}) = \frac{1}{2}\sum_i (y_i - (C^i_{first}P_i * X_{first} + C^i_{second}P_i * X_{second}))^2 + \beta(\|X_{first}\|_{TV} + \|X_{second}\|_{TV})$$

to obtain an equation in which a partial derivative of ψ with respect to $X_{first}^{r+1}(j)$ is equal to 0:

$$\sum_i C^i_{first}P_{ij}(y_i - (C^i_{first}P_i * X_{first}^r + C^i_{second}P_i * X_{second}^r)) + (X_{first}^r(j) - X_{first}^{r+1}(j))\sum_i (C^i_{first}P_{ij})^2 - \beta\frac{\partial \|X_{first}^r\|_{TV}}{\partial X_{first}^{r+1}(j)} = 0;$$

assuming $$\theta_1^{first} = \sum_i C^i_{first}P_{ij}(y_i - (C^i_{first}P_i * X_{first}^r + C^i_{second}P_i * X_{second}^r)),$$

$$\theta_2^{first} = \sum_i (C^i_{first}P_{ij})^2,$$

where $P_{ij}$ is a projection coefficient in the $i^{th}$ row and the $j^{th}$ column of the projection matrix P;

calculating $\theta_1^{first}$ and $\theta_2^{first}$, under the conditions that $P_{i*}X_{first}^r$ equals the i$^{th}$ row of the projection data a $q_{first}^r$ and $P_{i*}X_{second}^r$ equals the i$^{th}$ row of the projection data $q_{second}^r$;

calculating $X_{first}^{r+1}(j)$ from $$\theta_1^{first} + \theta_2^{first}(x_{first}^r(j) - X_{first}^{r+1}(j)) - \beta\frac{\partial \|X_{first}\|_{TV}}{\partial X_{first}} = 0$$

in a dichotomy method to update the pixel $X_{first}^{r+1}(j)$; and updating the orthographic projection data by $q_{first}^{r+1} = q_{first}^r + P \cdot (X_{first}^{r+1} - X_{first}^r)$;

the step of updating the $X_{second}^r$ comprises:

repeating the following steps until all pixels of $X_{second}^r$ are updated:

selecting one pixel $X_{second}^r(j)$ which is not updated in the $(r+1)^{th}$ iteration step, from the image vector $x_{second}^r$;

substituting $X_{second}^{r+1}(j)$ into the equation $$\psi(X_{first}, X_{second}) = \frac{1}{2}\sum_i (y_i - (C_{first}^i P_i * X_{first} + C_{second}^i P_i * X_{second}))^2 + \beta(\|X_{first}\|_{TV} + \|X_{second}\|_{TV})$$

to obtain an equation in which a partial derivative of $\psi$ with respect to $X_{second}^{r+1}(j)$ equals 0:

$$\sum_i C_{second}^i P_{ij}(y_i - (C_{first}^i P_i * X_{first}^r + C_{second}^i P_i * X_{second}^r)) +$$

$$(X_{second}^r(j) - X_{second}^{r+1}(j))\sum_i (C_{second}^i P_{ij})^2 - \beta\frac{\partial \|X_{second}^r\|_{TV}}{\partial X_{second}^{r+1}(j)} = 0$$

assuming $$\theta_1^{second} = \sum_i C_{second}^i P_{ij}(y_i - (C_{first}^i P_i * X_{first}^r + C_{second}^i P_i * X_{second}^r)),$$

$$\theta_2^{second} = \sum_i (C_{second}^i P_{ij})^2,$$

where $P_{ij}$ is a projection coefficient in the i$^{th}$ row and the j$^{th}$ column of the projection matrix P;

calculating $\theta_1^{second}$ and $\theta_2^{second}$ under the conditions that equals the i$^{th}$ row of the projection data $q_{first}^r$ and $P_{i*}X_{second}^r$ equals the i$^{th}$ row of the projection data $q_{second}^r$;

calculating $X_{Xsecond}^{r+1}(j)$ from $$\theta_1^{second} + \theta_2^{second}(x_{second}^r(j) - X_{second}^{r+1}(j)) - \beta\frac{\partial \|X_{second}\|_{TV}}{\partial X_{second}} = 0$$

in a dichotomy method to update the pixel $X_{second}^r(j)$, and updating the orthographic projection data by $q_{second}^{r+1} = q_{second}^r + P \cdot (X_{second}^{r+1} - X_{second}^r)$.

5. The method according to claim 4, wherein the output condition is $\|X_{first}^{r+1} - X_{first}^r\| < \epsilon$ and $\|X_{second}^{r+1} - X_{second}^r\| < \epsilon$, wherein $\epsilon$ is a preset small threshold.

6. The method according to claim 5, wherein the preset small threshold $\epsilon$ is at least less than $10^{-3}$.

7. The method according to claim 1, wherein the step of calculating respective combination coefficients $M^H_{first}$ and $M^H_{second}$ corresponding to the voltage values of the m sampling points according to m equations $M^H_{first}$ third-class image of first material $+M_{second}^H$ third-class image of second material $=$the $H^{th}$ second-class scan image is performed in a least square method.

8. A device of a reconstruction from a multi-energy CT scan, comprising:

a first data collecting unit adapted to set a first-class object comprising a first material and a second material as object to be scanned; perform data collection at a first-class voltage with a method for collecting multi-energy CT data, to collect n sets of first-class scan data $\{y_i\}$ in n projection angles, wherein i is an integer, $1 \le i \le n$, $n \ge 2$, the first-class voltage is varied periodically during the data collection, m different sampling points are distributed between a highest tube voltage and a lowest tube voltage of the first-class voltage, and performing the data collection at the first-class voltage comprises performing the data collection periodically at the voltages of the m sampling points during the data collection; and send the n sets of the first-class scan data $\{y_i\}$ to a multi-energy image reconstruction unit;

a second data collecting unit adapted to scan a double-cylinder correction phantom in n projection angles respectively, at the respective voltages of the m sampling points with the CT scanner, to obtain m groups of data, each group including n sets of second-class scan data, wherein the double-cylinder correction phantom comprises two materials to be discriminated in the first-class object, one cylinder comprises a first material, and the other cylinder comprises a second material; and send the m groups each including n sets of second-class scan data to a multi-energy correction unit;

the multi-energy correction unit adapted to reconstruct and correct m second-class scan images from the m groups of n sets of second-class scan data, wherein each group, including n sets of the second-class scan data, corresponds to one of reconstructed and corrected second-class scan images; obtain a third-class image vector of the first material and a third-class image vector of the second material according to the position and size of the first material and the second material in the double-cylinder correction phantom; calculate respective combination coefficients $M^H_{first}$ and $M^H_{second}$ corresponding to the voltage values of the m sampling points, according to m equations: $M^H_{first}$ third-class image vector of first material $+M^H_{second}$ third-class image vector of second material $=$the $H^{th}$ second-class scan image; and send the respective combination coefficients $M^H_{first}$ and $M^H_{second}$ corresponding to the voltage values of the m sampling points to the multi-energy reconstruction unit, where H is H$^{th}$ sampling point of the m tube voltage, H=0,1, . . . , m−1; and a multi-energy image reconstruction unit adapted to obtain image vectors $X_{first}$ and $X_{second}$ for which a difference between the first-class scan data $\{y_i\}$ and combination projection data $C^i_{first}P_{i*}X_{first} + C^i_{second}P_{i*}X_{second}$ has a minimum value, wherein $C^i_{first}$ and $C^i_{second}$ are combination coefficients corresponding to the case that the first-class scan data is collected at the first-class voltage in the i$^{th}$ projection angle, and $C^i_{first}$ and $C^i_{second}$ are obtained according to the respective combination coefficients $M^H_{first}$ and $M^H_{second}$ corresponding to the voltage values of the m sampling points, and $P_{i*}$ is the i$^{th}$ row of a projection matrix; determine the image vectors $X_{first}$ and $X_{second}$ for which a difference between the first-class scan data $\{y_i\}$ and the combination projection data $C^i_{first}P_{i*}X_{first}+C^i_{second}P_{i*}X_{second}$ has the minimum value, as the transpose of the first-class image vector of the first material and the transpose of the first-class image vector of the second material respectively;

a display unit adapted to display the reconstructed image.

* * * * *